United States Patent
Finkler

Patent Number: 6,028,314
Date of Patent: Feb. 22, 2000

[54] METHOD FOR CORRECTING IMAGE ERRORS IN AN X-RAY IMAGE, AND X-RAY DIAGNOSTIC APPARATUS AND SOLID-STATE RADIATION DETECTOR OPERATING IN ACCORDANCE WITH THE METHOD

[75] Inventor: Klaus Finkler, Spardorf, Germany

[73] Assignee: Siemens Aktiengesellschaft, Munich, Germany

[21] Appl. No.: 08/903,883

[22] Filed: Jul. 31, 1997

[30] Foreign Application Priority Data

Aug. 1, 1996 [DE] Germany ............... 196 31 137

[51] Int. Cl.$^7$ ........................... G01T 1/16
[52] U.S. Cl. ................ 250/370.11; 250/252.1; 250/363.09; 250/370.09; 250/371
[58] Field of Search .............. 250/370.09, 371, 250/370.11, 252.1 A, 363.09

[56] References Cited

U.S. PATENT DOCUMENTS 5,136,165  8/1992  Lumma ..................... 250/361 R
5,530,238  6/1996  Meulenbrugge et al. ........ 250/208.1

FOREIGN PATENT DOCUMENTS 1 122 114   5/1988   U.S.S.R. ............... 250/370.11
WO 96/16510  5/1996   WIPO .

Primary Examiner—Constantine Hannaher
Attorney, Agent, or Firm—Hill & Simpson

[57] ABSTRACT

In a method for correcting the image errors arising during an x-ray diagnostic measurement from the memory effect of a radiation-sensitive structure, particularly in the form of a photodiode array, of a solid-state detector which receiving the x-rays, given a change in the operating mode with a change of the radiation dose, a correction image is determined that is subtracted from the detector image obtained from the solid-state detector. For determining the correction image, at least one image signal supplied by the solid-state detector substantially immediately before or after the change in the operating mode, and thus the change of the radiation dose, is registered, this being subsequently weighted with at least one decay curve measured substantially synchronously with the pick-up of at least the image signal supplied immediately before the change, and substantially corresponding to the chronological decay behavior of the electrical charge in the radiation-sensitive structure of the solid-state detector of the image signal.

31 Claims, 5 Drawing Sheets

METHOD FOR CORRECTING IMAGE ERRORS IN AN X-RAY IMAGE, AND X-RAY DIAGNOSTIC APPARATUS AND SOLID-STATE RADIATION DETECTOR OPERATING IN ACCORDANCE WITH THE METHOD

BACKGROUND OF THE INVENTION

1. Field of the Invention

The invention is directed to a method for correcting image errors given a change in the operating mode, with a change in the radiation dose in the context of an x-ray diagnostic measurement, the method being of the type which makes use of the memory effect of a radiation-sensitive structure, particularly a photodiode array of a solid-state detector which receives the radiation, and wherein a correction image is obtained that is subtracted from the detector image obtained with the solid-state detector. The invention is also directed to an x-ray diagnostic apparatus and to a solid-state radiation detector operating according to the method.

2. Description of the Prior Art

Solid-state detectors are replacing the previously widely used film/screen systems. X-ray image intensifier/video chain systems are also currently utilized to an increasing extent in x-ray diagnostics. Such solid-state detectors, as employed, for example, in an image pick-up arrangement disclosed in PCT Application WO 96/16510, are constructed on the basis of a semiconductor component in which the radiation-sensitive structure is fashioned dependent on the type of solid-state detector. An exemplary embodiment of such a solid-state detector is photodiode matrix of amorphous silicon. The functioning of this solid-state detector is based on the generation of charge carriers when radiation is incident on one of the photodiodes fashioned in the semiconductor, the charge carriers being dependent on the type and intensity of the incident radiation. Since the photodiodes are usually sensitive only in a visible wavelength range, a scintillation layer, usually a cesium iodide layer, precedes the photodiodes for the conversion of the x-ray quanta, for which the photodiode is insensitive, into visible light.

The employment of such solid-state detectors has a number of advantages compared to the previously used systems, for example a small structural size and the low weight. Further, no high-voltage elements and phases are required; the power consumption is also lower. Such detectors also exhibit more significant contrast properties, but without the usual geometrical distortions arising therefrom.

A characteristic known as the memory effect, however, represents a significant problem associated with solid-state detectors. This effect is caused by charge carrier traps (often simply referred to as "traps") which are unavoidably formed in the semiconductor material and which capture a part of the charge carriers generated by the radiation exposure, and in turn release the trapped charge carriers over time due to energy activation, for example as a consequence of thermal events. This means that the charge carriers generated by a preceding exposure are not completely removed (or reset) in the following read-out cycle; on the contrary, a number of charge carriers remain trapped in the traps. These are only gradually removed in later read-out cycles and produce what is referred as a "residual image", which represents the cumulative effect of the gradually released charge carriers from a number of cycles. This occurs with every new image in a continuous sequence, so that the effects superimpose.

The memory effect is uncritical when image sequences are registered with a constant radiation dose, and thus with an electronic read-out amplification that also remains constant, since the residual image has already decayed to approximately 3% after about 160 ms; consequently, it makes only a negligible contribution to the following images. A correction of the effect then is not required for achieving an adequate image quality. When, by contrast, a sequence is operated with high radiation dose—which means that a number of charge carriers are generated as a consequence of the high dose, and consequently a low electronic read-out amplification is adequate, and a switch is made immediately thereafter to a low radiation dose (which involves a high electronic read-out amplification in order to achieve an adequate contrast), then a visible slowly decaying residual image can be observed that overlays the image sequence given the low dose. In this case, the decaying residual image that arises from the high exposure dose can still be as strong (visible) as the useful image generated by the low radiation dose up to a few seconds following the moment of switching. A correction is then essential in order to be able to utilize the image signals obtained immediately after the switch. Such an operating mode, namely the switch from a high to a low radiation dose, is very common in practice and is employed, for example, in order first to undertake a positioning of the patient or working device at a low radiation dose with low stress on the patient, for example in order to introduce a catheter into a coronary artery. The positioning can be adequately identified in a mode known as "fluoroscopic mode." After the positioning has been completed, the exposure mode is conducted using a high radiation dose, for example upon the addition of a contrast agent. For removing the catheter or for repositioning the catheter, for example, a switch is subsequently made back into the fluoroscopic mode with low radiation.

In order to correct the image errors arising from the memory effect, European Patent Application 0 642 264, for example, discloses a method wherein a correction image is continuously subtracted from the detector image, i.e. from the supplied image signal. This correction image is determined either based on a simulation of the physical events that are responsible for the memory effect and the decay of the charge carriers, or by pure calculation. The decay behavior, and thus the residual image, however, are dependent on a multitude of factors, for example on the dose, the time duration and the point in time of the preceding x-ray shots and, of course, also on the type of solid-state detector employed. Thus a correction using the method described in European Patent Application 0 642 264 is possible only with difficulty, particularly in the extreme range when switching the operating mode.

SUMMARY OF THE INVENTION

An object of the present invention is to provide an image correction method of the type initially described which enables the correction of the image errors caused by the memory effect upon a change of the radiation dose.

The above object is achieved in a method of the type initially described but wherein, in accordance with the invention an image signal supplied by the solid-state detector substantially immediately before or after the change in the operating mode, and thus a change in radiation dose, is registered for determining the correction image, this image signal being subsequently weighted with at least one decay curve that is measured substantially simultaneously with the pickup of at least the image signal which is supplied immediately before the change. The decay curve substantially corresponds to the decay behavior over time of the electrical charge corresponding to the image signal in the radiation-sensitive structure of the solid-state detector.

In the inventive method, thus, a correction image is generated by registering a specific image signal supplied at a time within a range on either side of the moment of switching modes and that corresponds to a carrier condition of the solid-state detector at that time, and by weighting this signal using a decay curve that is determined at substantially the same time and which corresponds to the charge carrier condition that exists in the solid-state detector immediately before the change. The decay curve thus represents a characteristic of the charge carriers generated at a high radiation dose and this decay behavior is continued in the following image sequence that is registered at a low radiation dose and which overlays the registered image signals of this sequence. The correction thus ensues directly with reference to a measured decay curve corresponding to the actual charge carrier condition immediately before the change, that is registered over a defined time span.

Inventively, an image signal generated given exposure with x-radiation is employed as the image signal registered before the change, and an image signal generated without exposure with x-radiation, i.e. a dark image, is employed as the image signal registered after the change. Consequently, two versions of the inventive method are disclosed. In a first version the correction image is generated based on at least one image signal supplied immediately before the change that is subsequently weighted with the decay curve associated therewith. Alternatively the correction image can be generated based on an image signal registered after the change of the radiation dose that is weighted with the decay curve corresponding to the high-dose charge state before the change. In this case, the later image signal must be registered as a dark signal, so that this image signal is a quasi-representation of the momentary dark charge carrier, i.e. it ultimately represents the charges that are trapped as a consequence of the memory effect and only flow off with a chronological delay. Dependent on which of these various image signals is employed, a correction image is obtained that is subtracted during the course of correction from the detector image obtained at a low radiation dose, so that image errors caused by the memory effect can be corrected in each of the method versions.

In a further version of the invention the decay curve is determined during the course of a reference measurement. This means that, according to the present method, no simulation or calculation is used as the basis of the correction, but instead correction based on a real measurement. Inventively, this reference measurement can be made by irradiating a radiation-sensitive structure comparable to the radiation-sensitive structure of the solid-state detector with light from a light source emitting visible light. The output signal of the optically irradiated solid-state structure corresponding to the momentary charge condition is measured for determining the decay curve. Thus, a reference measurement region is employed that is similar to the image-sensitive region of the solid-state detector in terms of its physical or measurable parameters. In parallel with the irradiation of the solid-state detector, thus, the reference measurement region is also irradiated, so that charge carriers are generated therein in a manner synchronized with the generation of charge carriers in the solid-state detector, and a corresponding charge condition thus is produced in the measurement region. Since the reference measurement region also supplies a corresponding output signal dictated by the charge condition, the decay curve of this charge condition, which is comparable to that existing in the solid-state detector, can be simply registered on the basis of the output signal and the decay curve can be determined with reference thereto. It has proven particularly expedient to employ a part of the radiation-sensitive structure of the solid-state detector itself as the reference measurement region, i.e. the reference region is fashioned directly at the solid-state detector itself. Alternatively, the reference measurement region can be an external (separate) radiation-sensitive structure.

To insure that the charge condition generated in the radiation-sensitive structure of the reference measurement region substantially corresponds to the actual charge condition present in the solid-state detector, in a further version of the invention the light source is triggered synchronously with a generator that generates the x-radiation, thereby achieving the same time parameters in the detector region and the reference region with respect to the generation of the charge carriers. As a result of triggering the light source irradiating the reference measurement region on the basis of the generator signal, namely, the light source becomes active at that moment when the generator is also activated, light quanta as well as x-ray quanta are applied to the respective radiation-sensitive regions parallel in time and consequently charge carriers are respectively generated in the regions parallel in time.

Since, as already initially described, the intensity of the emitted light has an influence on the number of generated charge carriers and since different decay behaviors are possible at different intensities as a consequence of this different generation behavior, in a further version of the invention the intensity of the light emitted by the light source is proportional to the dose of the x-radiation. Preferably, the light source intensity is coupled to the x-radiation intensity, so that it is assured that both regions are irradiated with comparable defined intensities and accordingly, a comparable generation behavior is realized. The control of the light source synchronously with the x-ray pulses and proportional to the dose results in the photodiodes of the reference measurement region being exposed with the same time parameters and intensity conditions as the photodiodes of the radiation-sensitive structure of the solid-state body. As a result, an output signal of the reference region is obtained that corresponds to the decay behavior in the image region of the solid-state detector.

Using only a single measurement region, one also obtains only a single decay curve is obtained. This assumes that the decay behavior of the photodiodes is the same in all radiation dose ranges. If, however, this is not the case, i.e. when a different decay behavior occurs in regions, for example, given a lower, applied x-radiation dose and given a higher, applied dose and, consequently, when the decay curves of these image locations differ greatly from one another with different exposure dose, a number of reference measurement regions would have to be provided. This means separate reference measurement regions would have to be respectively allocated to each such image location. In a detector wherein locally different decay behaviors over time respectively occur with locally different radiation doses in the radiation-sensitive structure of the solid-state detector, a number of decay curves are determined in accordance with the invention. This can be accomplished by using a number of reference measurement regions with corresponding light sources, these different regions being allocated during the course of the weighting to the corresponding, local regions that can be defined on the basis of the gray-scale values of the registered image signal. The proportionality factor employed for the intensity control of the respective light sources, allocated on a one-to-one basis with the reference measurement regions, can be inventively selected dependent on the "local" decay behavior of the particular region of the radiation-sensitive structure to which the respective decay curve is to be allocated. Thus, the control in this version is also proportional to dose, but with different proportionality factors due to the relationship between the x-ray dose and the light source intensity. The decay curves for different radiation doses (and thus, brightnesses) are thus obtained during the image pick-up sequence, with the pixels of the image signal, dependent on their gray-scale value, being subsequently individually weighted with the appertaining decay curve.

In addition to the inventive method, the invention is also directed to an x-ray diagnostics installation for implementation of the method, having a solid-state detector with a radiation-sensitive structure that is irradiated with a radiation emitted by a generator-operated source, an image memory communicating with the detector for storing image signals corresponding to the detector image, and a correction unit for correction of the image error arising from the memory effect of the radiation-sensitive structure of the solid-state detector by subtraction of a determined correction image from the detector image. This inventive x-ray diagnostic installation also includes at least one reference measurement region that can be irradiated by at least one light source, this having a radiation-sensitive structure comparable to the radiation-sensitive structure of the solid-state detector. The reference measurement region supplies an output signal corresponding to its charge condition that is used for the determination of a decay curve substantially corresponding to the chronological decay behavior of the electrical charge in the radiation-sensitive structure of the solid-state detector for a substantially synchronously obtained image signal.

Inventively, the reference measurement region, as already set forth, can be part of the radiation-sensitive structure itself. The charge carriers in the reference measurement region, which is integrated in the detector, should be generated only by the light emitted by the light source but not from the x-rays which may be incident thereon nor by radiation generated by an intervening scintillation layer which may be present. To avoid such spurious activation of the reference measurement region, the reference measurement region can be made insensitive to the radiation emitted by the x-ray source, thereby assuring that a defined charge carrier generation controlled exclusively by the light source can be realized. For this purpose, a layer that absorbs x-ray, particularly a lead layer, can be inventively placed between the reference measurement region and the x-ray source, this layer preferably being arranged directly on the solid-state detector. The reference measurement region is thus extensively shielded with the lead layer.

Alternatively or in addition thereto, the solid-state detector can have a scintillation layer that converts the incident x-ray into radiation that can be absorbed by the radiation-sensitive structure only in the x-ray-sensitive region and this can be removed in the reference measurement region, or not even applied at all. In this case as well, only the radiation emitted by the light source is incident on the reference measurement region; and external x-ray radiation is blocked.

In order to avoid stray radiation effects, in accordance with the invention the reference measurement region can be shielded from the remainder of the solid-state detector; such as by the reference measurement region boundary being impermeable to light and/or x-ray radiation. This avoids, for example, radiation emitted by the scintillation layer which is scattered from striking the reference measurement region; and also avoids radiation emitted by the light source from striking the image region of the solid-state detector and thus falsifying the image signal.

As noted above, the reference measurement region can be integrated in the solid-state detector, can be a radiation-sensitive structure external of the solid-state detector. This alternative, which thus entails the complete removal of the measurement region from the detector array, is advantageous because the reference region can be arranged spatially separated from the detector array, i.e. outside the x-ray region, and can be encapsulated light-tight at an arbitrary location of the overall system. It is also advantageous that manipulation of the image pick-up array such as, for example, the lead covering or light and x-ray shieldings, can be foregone.

A number of reference measurement regions, possibly each with its own light source, can be integrated or externally provided. These are preferably arranged at the edge or in a corner of the detector if the reference measurement regions are integrated. The same is true if only a single integrated reference measurement region is employed.

Further, the light source, or each light source, can be reversibly connected or disconnected by a switch, i.e. the light source is automatically shut off, for example when switching from a high radiation dose to a low radiation dose, so that the exposure of the reference measurement region is accordingly ended and only the decaying output signal that indicates the changing charge carrier condition in the reference measurement region is measured.

The light source, or each light source, can be triggered synchronously with the voltage generator that operates the x-ray source in order to realize the above-described synchronism with the x-ray pulses. In order also to enable a dose-proportional control of the light sources, the intensity of the radiation emitted by the light source or light sources can be adjustable, possibly individually for each light source, proportional to the applied x-ray dose.

The invention is also directed to a solid-state detector for employment in an x-ray diagnostic installation as described above, the detector having a radiation-sensitive structure, preferably in the form of a photodiode array, and possibly a scintillation layer preceding this layer for converting the incident x-ray into radiation that can be absorbed by the radiation-sensitive layer. This solid-state detector has at least one x-ray-insensitive reference measurement region that is irradiated by at least one light source for generating electrical charges, and which supplies an output signal corresponding to its charge condition. This output signal is useable, as described above, for determining a decay curve substantially corresponding to the chronological decay behavior of the electrical charge in the radiation-sensitive structure of the x-ray-sensitive region of the solid-state detector resulting from an x-ray exposure for a substantially synchronously obtained image signal.

A layer that absorbs x-rays, particularly a lead layer, can be arranged in the region of the reference measurement region, preferably directly on the solid-state detector, in order to render this region insensitive to x-rays. Alternatively, the solid-state detector can have a scintillation layer which converts the incident x-rays into radiation that can be absorbed by the radiation-sensitive structure only in the x-ray-sensitive region. The reference measurement region can be shielded from the other region of the solid-state detector; such as by making the region boundary impermeable for light rays and/or x-rays.

DESCRIPTION OF THE PREFERRED EMBODIMENTS

Figure 1:
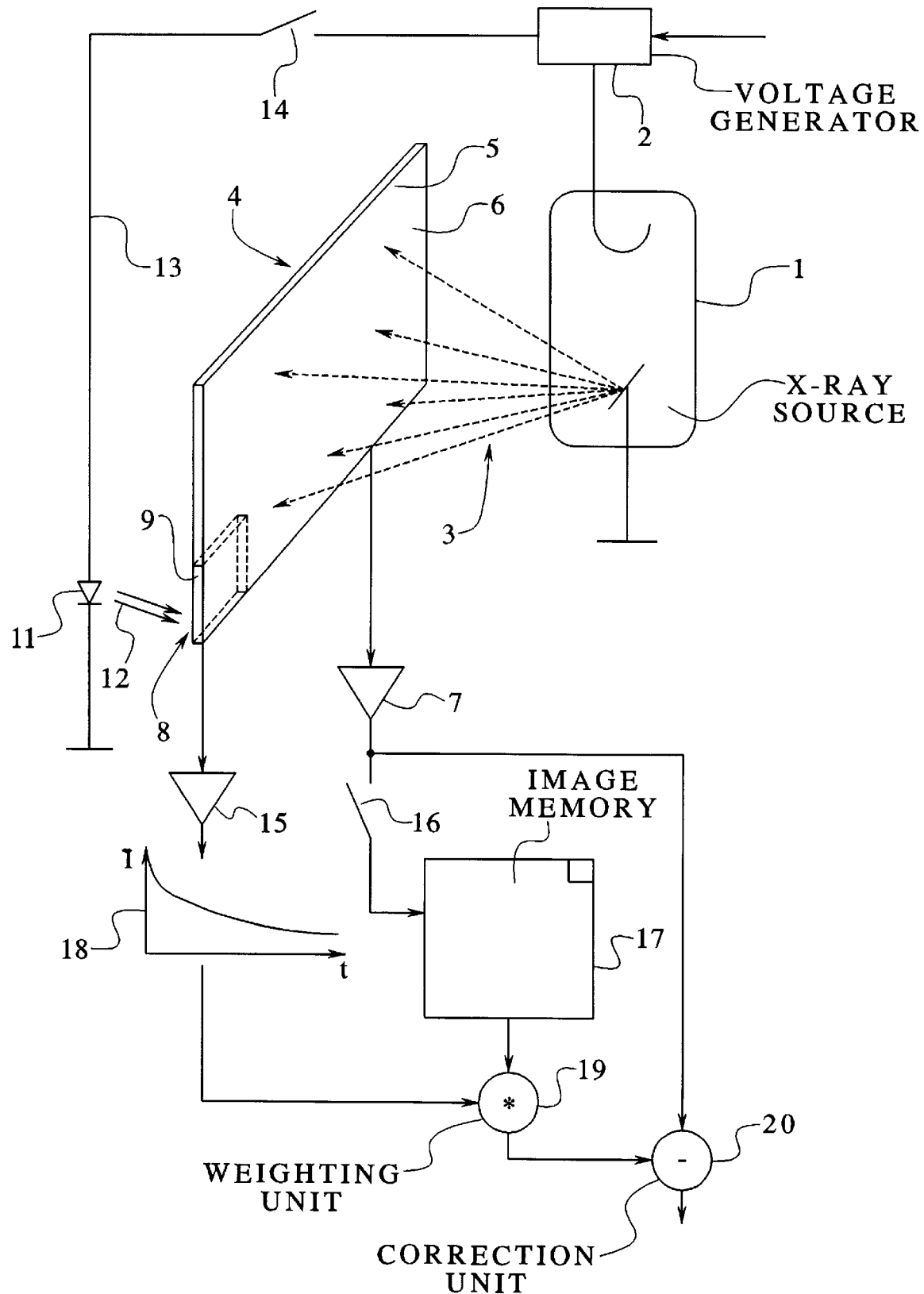
FIG. 1 is a schematic diagram that illustrates a first embodiment of the inventive method sequence and the structure of an x-ray diagnostics installation and a solid-state detector in accordance with the invention.

As shown in FIG. 1, x-rays 3 are generated by an x-ray source 1 dependent on a controlled voltage generator 2. The x-rays 3 strike a solid-state detector 4 after transirradiating a subject. This solid-state detector 4 has a region with a radiation-sensitive structure 5, for example in the form of a photodiode array, that is preceded by a scintillation layer 6. The scintillation layer 6 converts the x-rays 3, to which the radiation-sensitive 5 structure, for example, the photodiodes, are insensitive, into visible radiation that can be absorbed by the radiation-sensitive structure 5. Dependent on the intensity of the incident x-rays 3 and, consequently, on the intensity of the light radiation converted by the scintillation layer 6, charge carriers are generated in the individual photo-sensitive elements in the radiation-sensitive structure 5, the number of these charge carriers being dependent on the intensity. In this way, an image in the form of the charge carrier distribution is generated within the structure 5. The charges stored in the respective photodiodes, i.e. in the individual image pixels, can be read out for making the image visible, i.e. the solid-state detector supplies an image signal 7 that can be read out.

Figure 5:
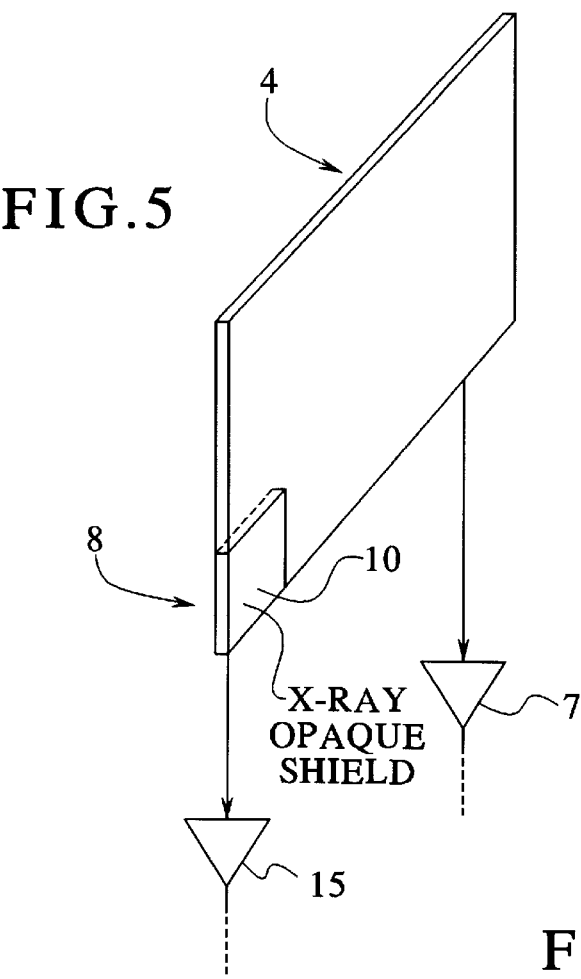
FIG. 5 shows the inventive solid-state detector of FIG. 1 in a modified version with an x-ray opaque shield.

As also shown in FIG. 1, a second region, a reference measurement region 8, is fashioned at the solid-state detector 4. This reference measurement region 8 likewise has a radiation-sensitive structure 9 that, since it is integrated, is the same as the radiation-sensitive structure 5 of the image-sensitive region of the solid-state detector 4. As shown in FIG. 5 a lead covering 10 can be arranged at that side of the reference measurement region 8 facing toward the x-ray source 3 in order to shield the structure 9 from the x-rays 3, so that this region 8 is insensitive for x-radiation. A light source 11 that emits light quanta 12 in the direction of the reference measurement region 8 is allocated to the reference measurement region 8. As shown by the connection 13, this light source 11 is connected to the voltage generator 2, and accordingly can be triggered by the voltage generator 2, i.e. its operation can be switched via the voltage generator 2. A switch 14 whose function is explained below is also provided. When the light source 11 illuminates the reference measurement region 8, charge carriers are also generated therein, and the charge condition in the form of an output signal 15 can also be read out from the region 8. In the illustrated example, the light source 11 irradiates the reference measurement region 8 from the rear of the solid-state detector 4; this is possible since the photodiode matrix is applied on a glass plate.

When the x-ray diagnostic installation is operated in pick-up mode, i.e. using a high x-ray dose in order to obtain an exact image of the structure to be transirradiated, the switch 14 is closed, causing the light source 11 to emit light quanta controlled by the voltage generator 2 synchronously in time and conforming in intensity with the x-rays 3. This allows an output signal 15 to be read out from the region 8. An image signal can also be read out parallel thereto since, of course, x-rays 3 are also applied. Via a further switch 16, this image signal is supplied to an image memory 17 in which it is stored. The switch 16 is closed in the operating mode with high radiation intensity, i.e. the image signal is deposited in the image memory 17. When a change in mode is now implemented, i.e. a switch is made to a transillumination or fluoroscopic mode wherein employing a low x-ray dose, the switch 14 is opened, resulting the light source 11 being shut off. The output signal 15 supplied from the reference measurement region 8 decays slowly, as indicated by the decay curve 18. The decaying measured signal is registered as a decay curve, which is a characteristic for the decay behavior of the charge carriers generated synchronously within the structure 5 of the image-sensitive region of the solid-state detector 4. Charge carriers resulting from the high x-ray dose are likewise stored in the structure 5, which have not yet been removed after the readout of the last image signal 7 decay slowly, and consequently and superimposed on a subsequent image measured given a low radiation dose. These persisting charge carriers lead to an erroneous charge carrier distribution that does not correspond to the x-rays actually applied, so that it is necessary to correct the image signal 7 measured at the low radiation dose. To this end, the image signal registered in the image memory 17 immediately before the change in operating mode is read out from the image memory 17 and is weighted with the decay curve 18, in a weighting unit 19. As a result of this weighting, a time-coordinated correction image can be calculated that is subsequently compared to the image signal 7 determined at the low radiation dose. This image signal now is not supplied to the image memory 17 due to the opening of the switch 16, but is forwarded directly into a correction unit 20 and is subtracted from the image signal 7 in order to obtain a corrected image in this way.

Alternatively to the use of the image signal 7 obtained immediately before the change in operating mode as basis for the determination of the correction image, the switch 16 can remain closed after a change so that a dark image signal is deposited in the image memory 17, i.e. an image signal without the application of x-rays 3. This image signal then corresponds to the residual charge condition in the radiation-sensitive structure 5, i.e. to the actual charge carrier distribution that still persists from the most recent high-dose irradiation. This "dark image" is also subsequently weighted with the decay curve in the same way as described above in order to correct the respective image signal when irradiation is conducted using a low radiation dose.

Figure 2:
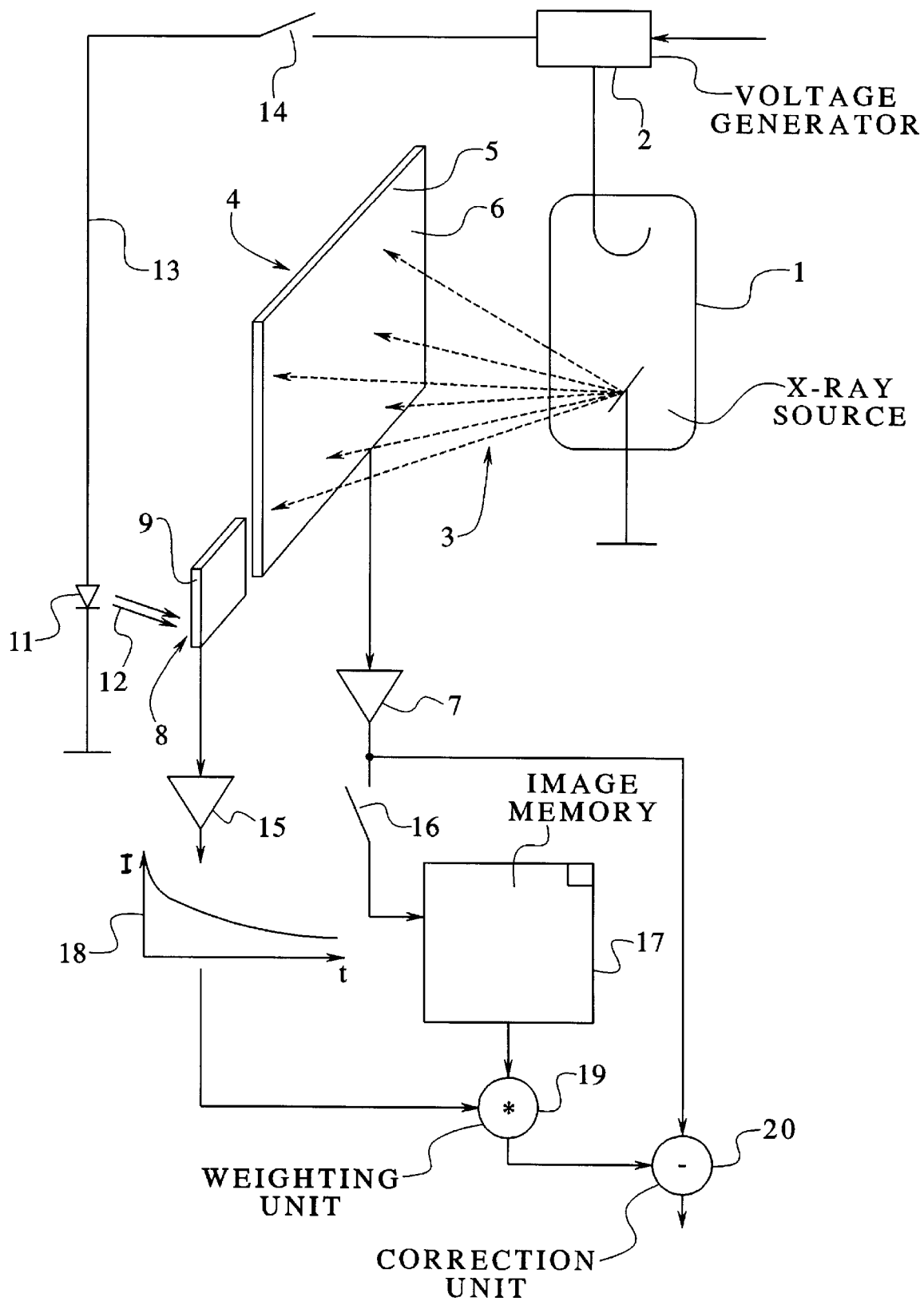
FIG. 2 is a schematic diagram that illustrates a second embodiment of the inventive method sequence and the structure of an x-ray diagnostics installation and a solid-state detector in accordance with the invention.

FIG. 2 shows an embodiment wherein the radiation-sensitive structure 9 which forms the reference measurement region 8 is separate from the radiation-sensitive structure 5 forming the solid-state detector 4. Otherwise, the structure and operation of the embodiment of FIG. 2 is the same as described above for the embodiment of FIG. 1, and therefore identical reference numerals have been used to identify the same components as in the embodiment of FIG. 1.

Figure 6:
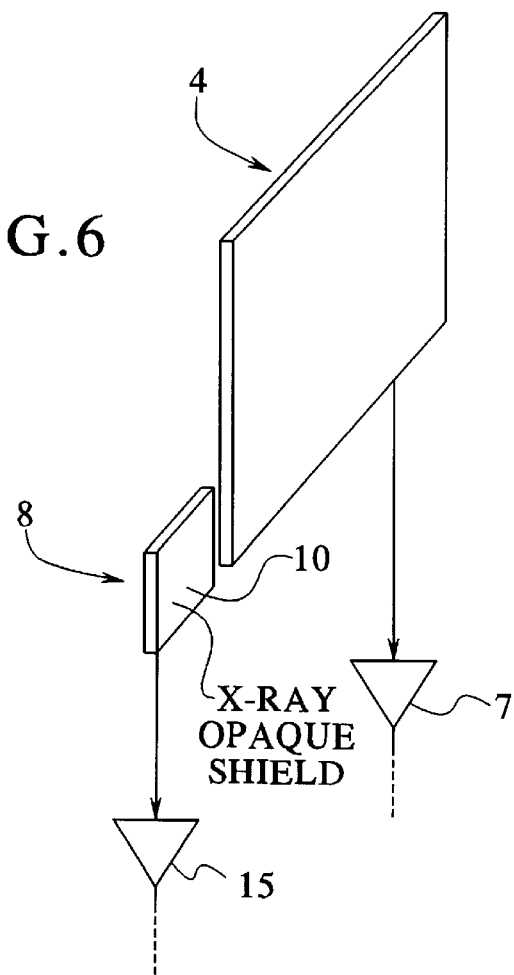
FIG. 6 shows the inventive solid-state detector of FIG. 2 in a modified version with an x-ray opaque shield.

FIG. 6 shows a lead covering 10 at that side of the separate radiation-sensitive structure 9 facing toward the x-ray source 3 in order to shield the structure 9 from the x-rays 3.

Figure 3:
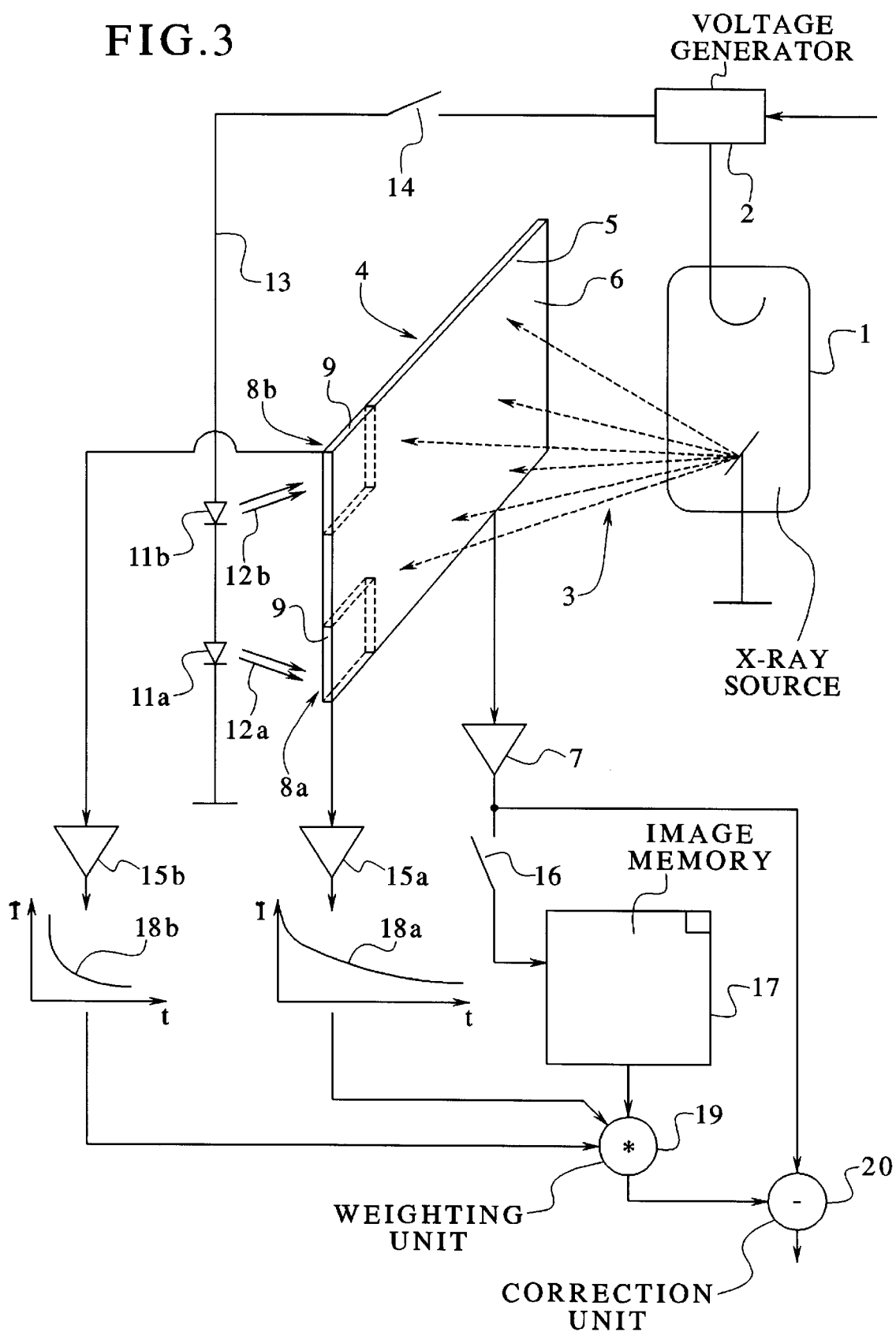
FIG. 3 is a schematic diagram that illustrates a third embodiment of the inventive method sequence and the structure of an x-ray diagnostics installation and a solid-state detector in accordance with the invention.

FIG. 3 illustrates an embodiment employing a number of reference measurement regions, namely two reference measurement regions 8a and 8b. The reference measurement region 8a is irradiated by optical radiation 12a emitted by a light source 11a, and the reference measurement region 8b is irradiated by optical radiation 12b emitted by a light source 11b. The respective reference measurement regions 8a and 8b exhibit different decay behavior, as indicated by the different decay curves 18a and 18b. Signals representing these curves are present at the respective outputs of amplifiers 15a and 15b, and both output signals are supplied to the weighting unit 19.

Figure 4:
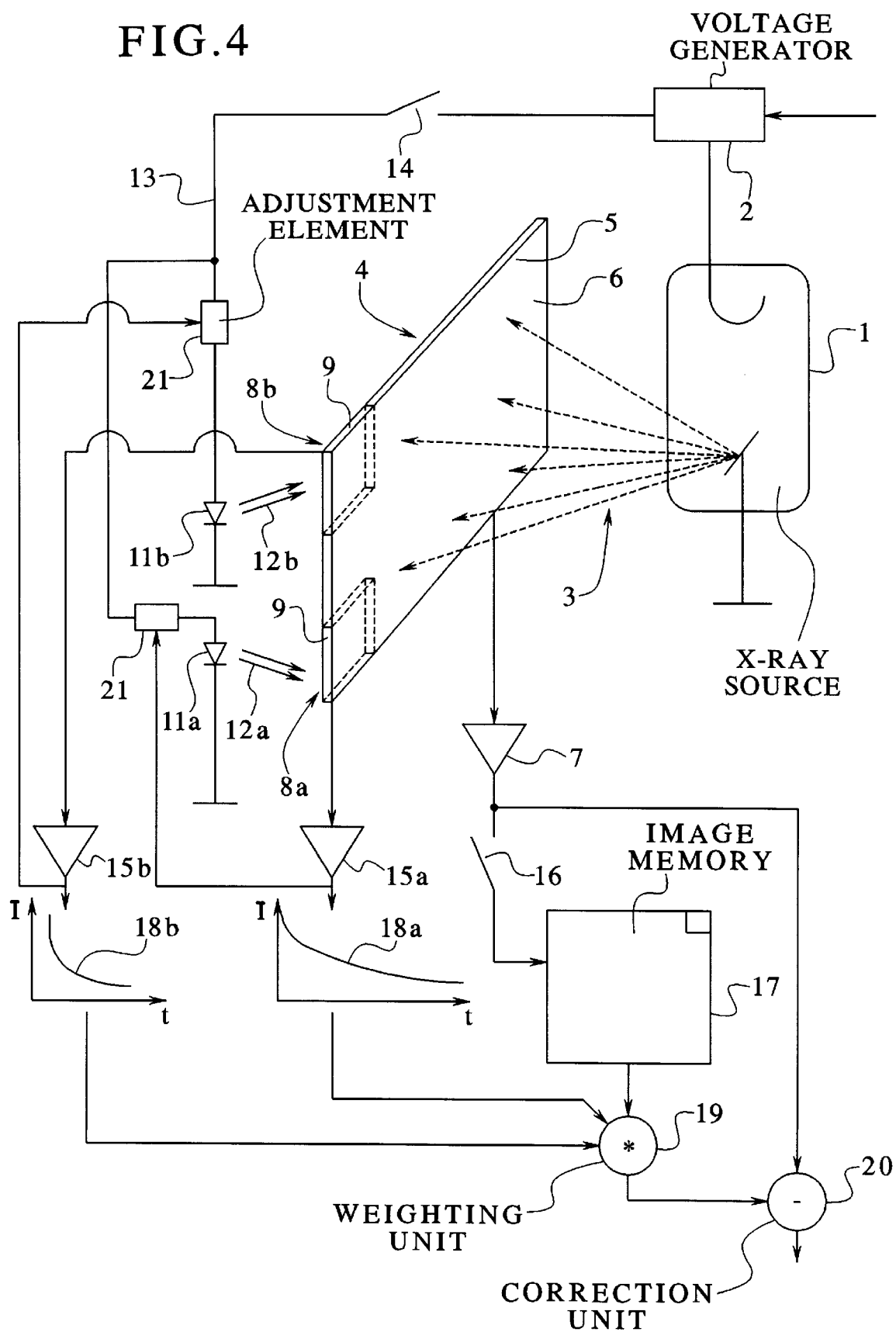
FIG. 4 is a schematic diagram that illustrates a fourth embodiment of the inventive method sequence and the structure of an x-ray diagnostics installation and a solid-state detector in accordance with the invention.

FIG. 4 shows a further embodiment similar to the embodiment of FIG. 3, wherein the output of the amplifier 15a is used to adjust the intensity of the optical radiation 12a emitted by the light source 11a, and the output of the amplifier 15b is used to adjust the intensity of the optical radiation 12b emitted by the light source 11b. This adjustment takes place via respective adjustment elements 21 of any suitable type.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for correcting image errors in an image produced by a penetrating radiation-sensitive detector, comprising the steps of:

providing a penetrating radiation-sensitive detector having a scintillator on which said penetrating radiation is incident, and a solid-state photodetector which produces a detector image from light generated by said scintillator due to penetrating radiation being incident thereon, said penetrating radiation-sensitive detector having a memory effect due to persisting charge carriers therein exhibiting a chronological decay behavior;

irradiating said penetrating radiation-sensitive detector with a first penetrating radiation dose;

changing said first penetrating radiation dose, at a change time, to a second penetrating radiation dose and producing a detector image from said penetrating radiation-sensitive detector at said second penetrating radiation dose;

producing a correction image from said penetrating radiation-sensitive detector at least at a time before said change time;

providing a reference measurement detector comprising an optical radiation-sensitive detector having a chronological decay behavior comparable to the chronological decay behavior of said solid-state photodetector;

providing a reference measurement optical radiation source;

measuring a decay curve, representing said chronological decay behavior, from said penetrating radiation-sensitive detector synchronously with producing said correction image by optically irradiating said reference measurement detector with optical radiation from said reference measurement optical radiation source to obtain a decay curve from said reference measurement detector and using said decay curve from said reference measurement detector as said decay curve representing said chronological decay behavior of said solid-state photodetector;

weighting said correction image with said decay curve to obtain a weighted correction image; and correcting said detector image produced at said second penetrating radiation dose by subtracting said weighted correction image therefrom.

2. A method as claimed in claim 1 wherein the step of producing said correction image comprises producing said correction image by irradiating said penetrating radiation-sensitive detector with penetrating radiation.

3. A method as claimed in claim 1 wherein the step of producing said correction image comprises producing said correction image without exposing said penetrating radiation sensitive detector to penetrating radiation.

4. A method as claimed in claim 1 wherein the step of providing a reference measurement detector comprises using a region of said solid-state photodetector as said reference measurement detector.

5. A method as claimed in claim 1 wherein the step of providing a reference measurement detector comprises providing a reference measurement detector separate from said solid-state photodetector.

6. A method as claimed in claim 1 wherein the step of irradiating said reference measurement detector comprises triggering said reference measurement optical radiation source synchronously with producing said correction image.

7. A method as claimed in claim 1 wherein the step of irradiating said reference measurement detector comprises irradiating said reference measurement detector with optical radiation from said reference measurement optical radiation source which is substantially proportional to said second penetrating radiation dose.

8. A method as claimed in claim 4, wherein said chronological decay behavior of said solid-state photodetector comprises a plurality of locally different chronological decay behaviors dependent on locally different respective radiation doses, and wherein the step of measuring said decay curve is conducted in a reference measurement, said reference measurement comprising the steps of:

providing a plurality of different reference measurement detectors respectively comprising optical radiation-sensitive detectors respectively exhibiting chronological decay behaviors comparable to one of said locally different chronological decay behaviors;

providing a plurality of reference measurement optical radiation sources;

respectively irradiating said radiation measurement detectors with optical radiation from said plurality of reference measurement optical radiation sources and obtaining a decay curve from each of said reference measurement detectors; and wherein the step of weighting said correction image with said decay curve comprises weighting said correction image with the different decay curves respectively obtained from said plurality of reference measurement detectors.

9. A method as claimed in claim 8 wherein each of said reference measurement optical radiation sources emits optical radiation at an intensity, and wherein said reference measurement comprises the additional step of respectively controlling the intensities of said reference measurement optical radiation sources dependent on the respective decay behaviors of said reference measurement detectors.

10. An arrangement for correcting image errors in an image produced by a penetrating radiation-sensitive detector, comprising:

a penetrating radiation-sensitive detector, said penetrating radiation-sensitive detector having a memory effect due to persisting charge carriers therein exhibiting a chronological decay behavior;

means for irradiating said penetrating radiation-sensitive detector with a first penetrating radiation dose;

means for changing said first penetrating radiation dose, at a change time, to a second penetrating radiation dose and producing a detector image from said penetrating radiation-sensitive detector at said second penetrating radiation dose;

means for producing a correction image from said penetrating radiation-sensitive detector at least at a time before said change time;

means for measuring a decay curve of a reference measurement region which is a part of said penetrating radiation-sensitive detector, said decay curve representing said chronological decay behavior, synchronously with producing said correction image;

means for weighting said correction image with said decay curve to obtain a weighted correction image; and means for correcting said detector image produced at said second penetrating radiation dose by subtracting said weighted correction image therefrom.

11. An arrangement as claimed in claim 10 wherein said measurement region comprises a part of said penetrating radiation-sensitive detector which is insensitive to said penetrating radiation.

12. An arrangement as claimed in claim 11 further comprising a layer which absorbs said penetrating radiation disposed between said reference measurement region and a remainder of said penetrating radiation-sensitive detector.

13. An arrangement as claimed in claim 10 wherein said penetrating radiation-sensitive detector comprises a scintillation layer which converts penetrating radiation incident thereon into optical radiation, and a solid-state photodetector which produces said detector image dependent on said optical radiation.

14. An arrangement as claimed in claim 10 wherein said penetrating radiation-sensitive detector, including said reference measurement region, comprises a scintillation layer which emits optical radiation dependent on penetrating radiation incident thereon, and a solid-state photodetector which produces said detector image dependent on said optical radiation from said scintillator layer, said solid-state photodetector exhibiting said chronological decay behavior, and wherein said means for measuring a decay curve comprises a reference measurement optical radiation source for irradiating said reference measurement region with optical radiation for measuring a decay curve from said reference measurement region for use as said decay curve representing said decay behavior of said solid-state photodetector.

15. An arrangement as claimed in claim 14 comprising a shield separating said reference measurement region from a remainder of said penetrating radiation-sensitive detector, said shield being impermeable to light and said penetrating radiation.

16. An arrangement as claimed in claim 14 comprising means for triggering said reference measurement optical radiation source synchronously with production of said correction image.

17. An arrangement as claimed in claim 14 wherein said optical radiation of said reference measurement optical radiation source has an intensity, and further comprising means for controlling said intensity of said optical radiation of said reference measurement optical radiation source dependent on said second penetrating radiation dose.

18. An arrangement as claimed in claim 10 wherein said penetrating radiation-sensitive detector comprises a scintillation layer which emits optical radiation dependent on penetrating radiation incident thereon and a solid-state photodetector which produces said detector image dependent on said optical radiation from said scintillation layer, said solid-state photodetector exhibiting said chronological decay behavior and said chronological decay behavior comprising a plurality of locally different chronological decay behaviors, and said arrangement comprising:

a plurality of optical radiation-sensitive reference measurement regions of said penetrating radiation-sensitive detector respectively exhibiting decay behaviors comparable to said locally different decay behaviors;

a plurality of reference measurement optical radiation sources for respectively irradiating said reference measurement regions with optical radiation, said reference measurement regions respectively generating different decay curves;

means for respectively measuring said different decay curves; and wherein said means for weighting said correction image comprises means for weighting said correction image with said plurality of different decay curves respectively measured from said plurality of reference measurement regions.

19. An arrangement as claimed in claim 18 wherein said locally different decay behaviors of said solid-state photodetector are dependent on locally different penetrating radiation doses, wherein each of said reference measurement optical radiation sources emits optical radiation at an intensity, and wherein said means for measuring a decay curve further comprises means for respectively controlling the intensities of said reference measurement optical radiation sources dependent on said locally different penetrating radiation doses.

20. A solid-state detector for penetrating radiation comprising:

a scintillation layer which emits optical radiation dependent on penetrating radiation incident thereon;

a solid-state photodetector which generates a detector image dependent on said optical radiation from said scintillation layer, said solid-state photodetector having a memory effect due to persisting charge carriers therein exhibiting a chronological decay behavior;

said solid-state photodetector having a penetrating radiation-insensitive reference measurement region which, when irradiated by an optical radiation source, generates charge carriers exhibiting a chronological decay behavior comparable to said chronological decay behavior of a remainder of said penetrating radiation-sensitive detector.

21. A solid-state detector as claimed in claim 20 further comprising a layer which absorbs said penetrating radiation disposed between said reference measurement region and said remainder of said solid-state photodetector.

22. A solid-state detector as claimed in claim 20 further comprising means for shielding said reference measurement region from a remainder of said solid-state photodetector, said means for shielding being impermeable to said penetrating radiation and to optical radiation.

23. A method for correcting image errors in an image produced by a penetrating radiation-sensitive detector, comprising the steps of:

providing a penetrating radiation-sensitive detector, said penetrating radiation-sensitive detector having a memory effect due to persisting charge carriers therein exhibiting a chronological decay behavior;

irradiating said penetrating radiation-sensitive detector with a first penetrating radiation dose;

changing said first penetrating radiation dose, at a change time, to a second penetrating radiation dose and producing a detector image from said penetrating radiation-sensitive detector at said second penetrating radiation dose;

producing a correction image from said penetrating radiation-sensitive detector, without exposing said penetrating radiation-sensitive detector to penetrating radiation, at least at a time before said change time;

measuring a decay curve, representing said chronological decay behavior, from said penetrating radiation-sensitive detector synchronously with producing said correction image;

weighting said correction image with said decay curve to obtain a weighted correction image; and correcting said detector image produced at said second penetrating radiation dose by subtracting said weighted correction image therefrom.

24. An arrangement for correcting image errors in an image produced by a penetrating radiation-sensitive detector, comprising:

a penetrating radiation-sensitive detector, said penetrating radiation-sensitive detector having a memory effect due to persisting charge carriers therein exhibiting a chronological decay behavior;

means for irradiating said penetrating radiation-sensitive detector with a first penetrating radiation dose;

means for changing said first penetrating radiation dose, at a change time, to a second penetrating radiation dose and producing a detector image from said penetrating radiation-sensitive detector at said second penetrating radiation dose;

means for producing a correction image from said penetrating radiation-sensitive detector at least at a time before said change time;

a reference measurement detector, separate from said penetrating radiation-sensitive detector;

means for measuring a decay curve of said reference measurement detector, said detector representing said chronological decay behavior, synchronously with producing said correction image;

means for weighting said correction image with said decay curve to obtain a weighted correction image; and means for correcting said detector image produced at said second penetrating radiation dose by subtracting said weighted correction image therefrom.

25. An arrangement as claimed in claim 24 wherein said penetrating radiation-sensitive detector comprises a scintillation layer which converts penetrating radiation incident thereon into optical radiation, and a solid-state photodetector which produces said detector image dependent on said optical radiation.

26. An arrangement as claimed in claim 24 wherein said penetrating radiation-sensitive detector comprises a scintillation layer which emits optical radiation dependent on penetrating radiation incident thereon, and a solid-state photodetector which produces said detector image dependent on said optical radiation from said scintillator layer, said solid-state photodetector exhibiting said chronological decay behavior, and wherein said reference measurement detector comprises an optical radiation-sensitive reference measurement detector having a chronological decay behavior comparable to the chronological decay behavior of said solid-state photodetector, and a reference measurement optical radiation source for irradiating said reference measurement detector with optical radiation for measuring a decay curve from said reference measurement detector for use as said decay curve representing said decay behavior of said solid-state photodetector.

27. An arrangement as claimed in claim 26 wherein said reference measurement detector has a side facing said means for irradiating, and said arrangement further comprising a shield covering said side of said reference measurement detector, said shield being impermeable to light and said penetrating radiation.

28. An arrangement as claimed in claim 26 comprising means for triggering said reference measurement optical radiation source synchronously with production of said correction image.

29. An arrangement as claimed in claim 26 wherein said optical radiation of said reference measurement optical radiation source has an intensity, and further comprising means for controlling said intensity of said optical radiation of said reference measurement optical radiation source dependent on said second penetrating radiation dose.

30. An arrangement as claimed in claim 26 wherein said penetrating radiation-sensitive detector comprises a scintillation layer which emits optical radiation dependent on penetrating radiation incident thereon and a solid-state photodetector which produces said detector image dependent on said optical radiation from said scintillation layer, said solid-state photodetector exhibiting said chronological decay behavior and said chronological decay behavior comprising a plurality of locally different chronological decay behaviors, and said arrangement comprising:

a plurality of optical radiation-sensitive reference measurement detectors respectively exhibiting decay behaviors comparable to said locally different decay behaviors;

a plurality of reference measurement optical radiation sources for respectively irradiating said reference measurement detectors with optical radiation, said reference measurement detectors respectively generating different decay curves;

means for respectively measuring said different decay curves; and wherein said means for weighting said correction image comprises means for weighting said correction image with said plurality of different decay curves respectively measured from said plurality of reference measurement detectors.

31. An arrangement as claimed in claim 30 wherein said locally different decay behaviors of said solid-state photodetector are dependent on locally different penetrating radiation doses, wherein each of said reference measurement optical radiation sources emits optical radiation at an intensity, and wherein said means for measuring a decay curve further comprises means for respectively controlling the intensities of said reference measurement optical radiation sources dependent on said locally different penetrating radiation doses.

* * * * *